(12) United States Patent
Finch et al.

(10) Patent No.: US 7,689,260 B2
(45) Date of Patent: Mar. 30, 2010

(54) SHAPE-MEMORY POLYMER COATED ELECTRODES

(75) Inventors: Dudley Finch, Boulder, CO (US);
Kenneth Gall, Boulder, CO (US);
Andrew Sharp, Boulder, CO (US);
Diego Restrepo, Boulder, CO (US)

(73) Assignee: The Regents of the University of Colorado, Boulder, CO (US)

( * ) Notice: Subject to any disclaimer, the term of this patent is extended or adjusted under 35 U.S.C. 154(b) by 388 days.

(21) Appl. No.: 10/577,962

(22) PCT Filed: Nov. 8, 2004

(86) PCT No.: PCT/US2004/037510

§ 371 (c)(1),
(2), (4) Date: Dec. 8, 2006

(87) PCT Pub. No.: WO2005/046470

PCT Pub. Date: May 26, 2005

(65) Prior Publication Data

US 2007/0073130 A1    Mar. 29, 2007

Related U.S. Application Data

(60) Provisional application No. 60/517,853, filed on Nov. 6, 2003, provisional application No. 60/526,553, filed on Dec. 3, 2003, provisional application No. 60/528,737, filed on Dec. 11, 2003.

(51) Int. Cl.
*A61B 5/04* (2006.01)
*A61N 1/05* (2006.01)

(52) U.S. Cl. ................ 600/378; 607/116

(58) Field of Classification Search ........... 600/377, 600/378; 607/116
See application file for complete search history.

(56) References Cited

U.S. PATENT DOCUMENTS

| | | | | |
|---|---|---|---|---|
| 4,258,724 A | * | 3/1981 | Balat et al. | 607/128 |
| 4,827,940 A | * | 5/1989 | Mayer et al. | 600/375 |
| 5,653,742 A | * | 8/1997 | Parker et al. | 607/137 |
| 6,091,979 A | * | 7/2000 | Madsen | 600/377 |
| 6,427,086 B1 | * | 7/2002 | Fischell et al. | 607/45 |
| 2003/0125786 A1 | * | 7/2003 | Gliner et al. | 607/116 |
| 2004/0006264 A1 | * | 1/2004 | Mojarradi et al. | 600/378 |
| 2005/0021117 A1 | * | 1/2005 | He et al. | 607/116 |

* cited by examiner

*Primary Examiner*—Lee S Cohen

(57) ABSTRACT

There is provided a slowly implantable electrode. A coating for an electrode, the coating includes a shape-memory polymer. A method for inserting an electrode into brain tissue by inserting an implantable electrode having a shape-memory polymer coated electrode into brain tissue.

7 Claims, 4 Drawing Sheets

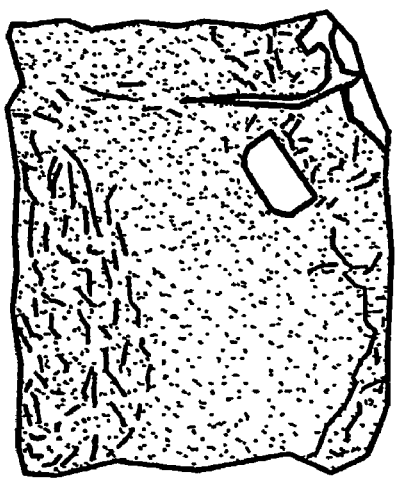
*FIG - 3a*  *FIG - 3b*
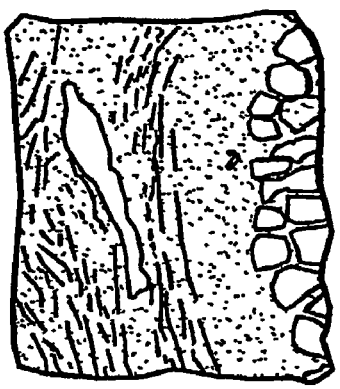
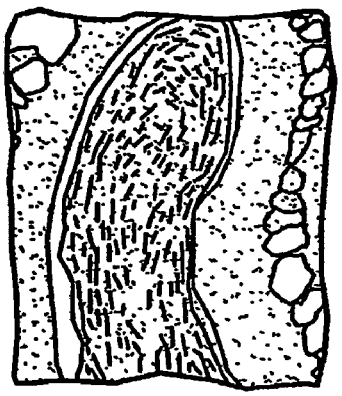
*FIG - 4a*  *FIG - 4b*
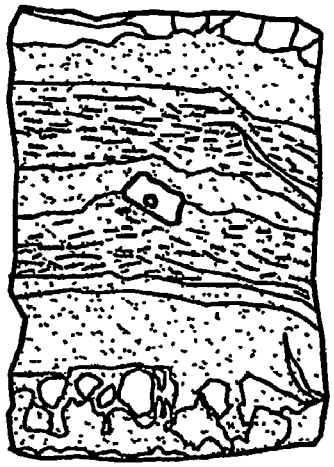
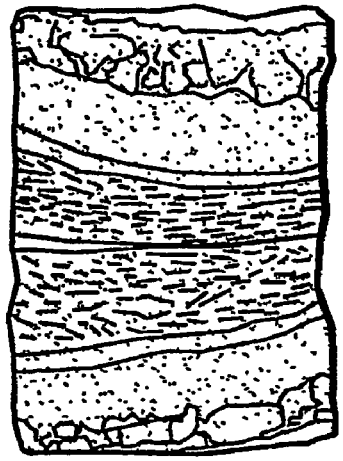
*FIG - 5a*  *FIG - 5b*

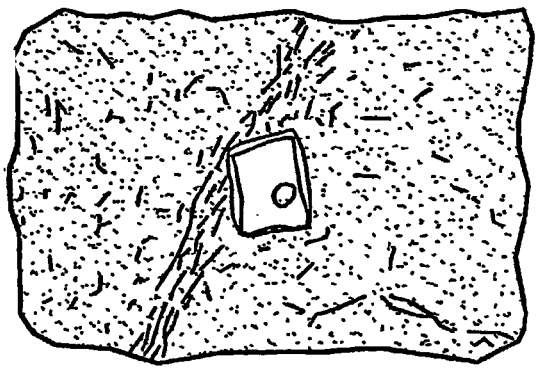
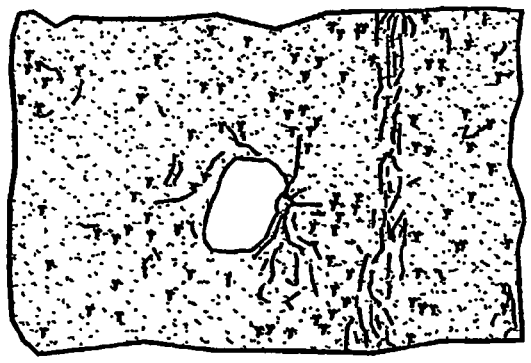

SHAPE-MEMORY POLYMER COATED ELECTRODES

CROSS-REFERENCE TO RELATED APPLICATIONS

This is a National Phase Filing Under 35 U.S.C. 371, of International Application No. PCT/US04/37510, filed Nov. 8, 2004, which claims the benefit of priority of U.S. Provisional Patent Application Ser. No. 60/517,853, filed Nov. 6, 2003; U.S. Provisional Patent Application Ser. No. 60/526,553, filed Dec. 3, 2003; and U.S. Provisional Patent Application No. 60/528,737, filed Dec. 11, 2003, all of which are incorporated herein by reference.

BACKGROUND OF THE INVENTION

1. Field of the Invention

Generally, the present invention relates to coated electrodes or other biosensors. More specifically, the present invention relates to electrodes capable of insertion into the brain, spinal cord or other tissue.

2. Description of Related Art

Systems for electrically monitoring and stimulating the brain and spinal cord are increasingly important in the medical diagnosis and treatment of various disorders, such as spinal cord injury, stroke, epilepsy, Parkinson's disease, sleep disorders, migraine, and psychiatric ailments. Therapeutic neurostimulatory devices can include one or more leads having at least one electrode operatively situated in the brain or other neural tissue and linked to a signal processor for detecting neurological activity and to a pulse generator for providing electrical stimuli.

For several years research has been conducted in attempts to establish communication with living neurons, to communicate to the human brain information which can no longer be provided by a person's own eyes or ears, to stimulate paralyzed muscles, to stimulate autonomic nerves, as to control bladder function or pace the heart, or to control prosthetic limbs.

It is well known that electrical stimulation of certain nerves and certain regions of the brain can be perceived consciously, and research is being performed with the intention of eventually learning how to stimulate nerves in ways that can provide useful information to a person whose ability to hear or to see has been lost. Indeed, cochlear implants have been used successfully to allow deaf individuals to detect sound. Further, recent work has been done with optical imaging for sight.

To utilize neural prostheses, electrical signals made by living neurons must be detected, typically by recording and/or stimulating extracellular field potentials. Such extracellular field potentials must be recorded with extremely small electrodes, in order to detect the small voltages created by transmembrane currents generated by neurons adjacent to the electrode tip. In addition to allowing detection of signals emitted by nerve cells, current can be injected through the electrode to provide stimulation to the nerves. To limit the mechanical trauma caused by insertion and chronic presence of electrode structures, the entire electrode structure and associated wires must be as small as possible consistent with the required ability to conduct electrical energy, and must be of materials which will not react deleteriously with the living body.

Implanted biosensors and conductors connected to them must be electrically insulated very effectively, because of the very small voltages that must be detected. The localized nature of the electrical potential gradient that must be detected by a microelectrode, and the fragility of neurons, dictate a microelectrode tip with small dimensions (typically less than 75 micrometers in diameter), which in turn produces a high impedance. Since the probe as a whole must have a slender profile to minimize disruption of tissue, the requirement to minimize shunt losses along the insulated shank of the probe falls on a very thin dielectric coating which must be cleanly excluded from the tiny exposed tip or window. Insulating coatings on conductors must be free from small holes and should be tightly adhered to the insulated wires and parts of electrodes. It is known that there are some biologically compatible dielectric materials that can be applied consistently and successfully as coatings of uniform thickness for such small structures as are found in microelectrodes to be used for neural prostheses. An insulating coating of Parylene-C™, a polymerized diparachloroxylyene produced by the Union Carbide Corporation, is known to have the required biological compatibility and electrical insulation qualities and can be applied successfully to electrode surfaces, but the techniques previously available for removing portions of such a coating have not been entirely satisfactory.

An additional problem associated with inserting foreign objects into the body, including prior art electrodes and biosensors is that the act of inserting the electrode into the brain causes damage to the brain tissue. Specifically, the insertion of the foreign object causes tissue inflammation and necrotic cell death. For example, in the brain a long-term reactive astrocytic reaction ensues that leads to physical blockage of an electrode by a surrounding sheath of reactive astrocytes. The sheath of reactive astrocytes limits the electrodes ability to receive signals from the surrounding neurons.

Current state of the art is to insert the electrodes quickly into brain tissue. The method of insertion has not been effective at eliminating the problem associated with the astrocyte sheath.

An additional problem with the implant that are currently being utilized is that of micromovement or micromotion of the tissue relative to the implant. Many individuals in the field have attributed persistent problems with poor biocompatibility to such micromovement.

It would therefore be beneficial to develop an electrode that, upon insertion into brain tissue does not cause formation of the sheath of reactive astrocytes and can overcome the above problems with regard to biocompatibility.

SUMMARY OF THE INVENTION

According to the present invention, there is provided a slowly implantable electrode. A coating for an electrode, the coating includes a shape-memory polymer. A method for inserting an electrode into body tissue by inserting an implantable electrode having a shape-memory polymer coated electrode into body tissues.

DESCRIPTION OF THE DRAWINGS

Other advantages of the present invention are readily appreciated as the same becomes better understood by reference to the following detailed description when considered in connection with the accompanying drawings wherein:

FIGS. 3A and 3B are photographs showing tissue response to implantation of 100×200 μm SMP one week post-implantation; the scale bar is 200 μm;

FIGS. 4A and 4B are photographs showing tissue response to implantation of 100×200 μm SMP after two weeks; the scale bar is 200 μm;

FIGS. 5A and 5B are photographs showing tissue response to a one week "slowly" (1 mm/40 minutes) inserted SMP/gold wire implant (75×200 μm);

FIG. 6A shows a digital micrograph of a SMP beam partially inserted into the olfactory bulb; and FIG. 6B is a force-displacement graph;

FIGS. 7A-7D are photographs showing two different designs (FIGS. 7A and 7B, and FIGS. 7C and 7D) for SMP linear actuators with 25 μm embedded gold wire in the compressed state ((FIG. 7A) and (FIG. 7C)) and following thermal actuation ((FIG. 7B) and (FIG. 7D)); bars are 1 mm;

FIGS. 8A and 8B are photographs showing the shape-memory effect in polyglycolic acid (PGA); FIG. 8A shows the shape after deformation at 120° C. and FIG. 8B shows the subsequent recovery above $T_g$; the bar is 1 mm; and FIGS. 9A and 9B are photographs that show the astrocytosis observed one month after implantation of a smp and silicon beam respectively. The epoxy smp beam generated negligible astrocytosis while the silicon beam generated a significant astrocytic response. The magnitude of the response to silicon appears less than that shown in the prior art. This is due to a reduction in micro-movement of the beam since it is not connected to a large array. Scale bar equals 100 μm.

DETAILED DESCRIPTION OF THE INVENTION

Figure 1A:
FIG. 1 is a schematic of the shape-memory effect in polymers as defined by four critical temperatures.
Figure 1B:
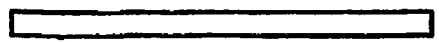
Figure 1C:
Figure 1D:
Figure 1E:
Figure 1F:

Generally, the present invention provides shape-memory polymers (SMP) with embedded single or multiple microwire or nanowire conductors. The shape-memory polymers and the embedded alloys can be used as electrodes that can be used for long-term recording and/or stimulation in different tissues in the body. The SMP electrodes and the embedded wires are capable of deployment at slow rates (minutes to days) post-implantation thereby minimizing adverse tissue reactivity. SMP electrodes operate on the principle of using low modulus materials to better match the mechanical properties of tissue.

Slow deployment (minutes to days) of electrodes through thermal actuation of shape-memory polymers (SMP's) greatly diminishes the inflammatory astrocytic scar reaction that adversely affects long-term electrode performance. The electrodes of the present invention are capable of being deployed slowly because of the use of coatings on the exterior surface of the electrode. The coatings enable the electrodes to be more biocompatible. The use of a bioresorbable coating on the exterior surface of the electrode also decreases micromovement, thereby increasing the biocompatibility of the electrode. Micromovement is decreased because the coated electrode is "suspended" in the tissue. The "suspension" makes the electrode less prone to movement. Additionally, the use of a bioresorbable coating adjacent the backing of an array can be used to "free" an electrode from the mass associated from the array backing.

The term "tissue" as used herein is intended mean an aggregate of cells having a similar structure and function. Examples of tissues include, but are not limited to, brain tissue, the spinal cord and bodily organs.

The term "bioresorbable coating" as used herein is intended to mean a coating containing therein material that is capable of being absorbed by the tissue into which the coating is inserted. Examples of such coatings are well known to individuals of skill in the art.

An "electrode" is a generalized biosensor or biostimulatory device. For example, such an electrode can be used to measure field potentials, chemicals, including neurotransmitters and metabolites, pH or protein concentration. Such an electrode can also be used to stimulate tissue in different ways, including electrical and chemical stimulation, temperature, pressure, and flow. The electrode can be formed of any material known to those of skill in the art. Examples of such materials include, but are not limited to, polymers and gold as these compounds have greater compliance. However, other materials can also be utilized without departing from the spirit of the present invention.

With regard to the electrodes, a micro-electro-mechanical system (MEMS) can be used to position electrodes prior to final deployment of the electrode, prior to the occurrence of the shape-memory effect. Additionally, MEMS can be used to fine-tune the placement of the electrode post-deployment or insertion.

The micro-electro-mechanical system (MEMS) utilizes thin film materials deposited on a silicon substrate typically 500 micrometers in thickness. The materials used to fabricate MEMS devices are at least several micrometers thick, and are typically formed using processing methods such as casting, sol-gel technology, spin coating, micromachining to selectively etch parts of the silicon wafer and addition of new structural layers using photoresist and photomasking techniques. MEMS provides the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components are fabricated using compatible "micromachining" processes that selectively etch away parts of the silicon wafer or add new structural layers to form the mechanical and electromechanical devices.

MEMS brings together silicon-based microelectronics with micromachining technology, making possible the realization of complete systems-on-a-chip. MEMS is an enabling technology allowing the development of smart products, augmenting the computational ability of microelectronics with the perception and control capabilities of microsensors and microactuators and expanding the space of possible designs and applications.

Microelectronic integrated circuits can be thought of as the "brains" of a system and MEMS augments this decision-making capability with "eyes" and "arms", to allow microsystems to sense and control the environment. Sensors gather information from the environment through measuring mechanical, thermal, biological, chemical, optical, and magnetic phenomena. The electronics then process the information derived from the sensors and through some decision making capability direct the actuators to respond by moving, positioning, regulating, pumping, and filtering, thereby controlling the environment for some desired outcome or purpose. Because MEMS devices are manufactured using batch fabrication techniques similar to those used for integrated circuits, unprecedented levels of functionality, reliability, and sophistication can be placed on a small silicon chip at a relatively low cost.

Another processing method, the electrostatic self-assembly ("ESA") method, has been widely used to synthesize multifunctional high performance materials and devices. This low-cost process offers a number of advantages over conventional film synthesis techniques to form layer-by-layer composite films with excellent molecular-level uniformity and precise structural control. For example, U.S. Pat. No. 5,208, 111 describes one- or multi-layered elements applied to supports that are produced by applying the individual layers from solutions of organic materials in suitable solvents to modified supports by sequential physiosorption (salt formation).

U.S. Pat. No. 6,020,175 also employs the ESA method, and describes the fabrication of thin films which include multiple layers of functional molecules (such as enzymes and other proteins, pigments and dyes) admixed with polymer ions in combination with multiple layers of polymer ions without the functional molecules.

A polymer is a shape-memory polymer if the original shape of the polymer is recovered by heating it above a shape recovering temperature (defined as the $T_{trans}$ or $T_r$) even if the original molded shape of the polymer is altered mechanically at a lower/higher temperature than the shape recovering temperature, or if the memorized shape is recoverable by application of another stimulus.

As used herein, the term "segment" refers to a block or sequence of polymer forming part of the shape-memory polymer.

As used herein, the terms hard segment and soft segment are relative terms, relating to the $T_{trans}$ of the segments. The hard segment(s) has a higher $T_{trans}$ than the soft segment(s).

As used herein, the term "biodegradable" refers to materials that are bioresorbable and/or degrade and/or break down by mechanical degradation upon interaction with a physiological environment into components that are metabolizable or excretable, over a period of time from minutes to years, preferably less than one year, while maintaining the requisite structural integrity. As used herein in reference to polymers, the term "degrade" refers to cleavage of the polymer chain, such that the molecular weight stays approximately constant at the oligomer level and particles of polymer remain following degradation. The term "completely degrade" refers to cleavage of the polymer at the molecular level such that there is essentially complete mass loss. The term "degrade" as used herein includes "completely degrade" unless otherwise indicated.

Shape-memory polymers can be thermoplastic, thermoset, interpenetrating networks, semi-interpenetrating networks, or mixed networks. Polymers can be a single polymer or a blend of polymers. Polymers can be linear, branched, thermoplastic elastomers with side chains or any kind of dendritic structural elements. Stimuli causing shape change can be temperature, ionic change, pH, light, electric field, magnetic field or ultrasound.

Shape-memory materials can be shaped (e.g. molded) to a desired shape above or slightly below the $T_{trans}$ of the hard segment(s) and cooled to a temperature below the shape recovering temperature. The original shape of the deformed polymers can be recovered by heating them to a temperature higher than their shape recovering temperature. Above this temperature, the strains in the polymer are relieved, allowing the polymer to return to its original shape.

When significant stress is applied, resulting in an enforced mechanical deformation at a temperature lower than the shape recovering temperature, strains are retained in the soft segments, or amorphous regions, and bulky shape change is kept even after the partial liberation of strain by the elasticity of the polymer.

In addition to changes in state from a solid to liquid state (melting point or glass transition temperature), hard or soft segments can undergo ionic interactions involving polyelectrolyte segments or supramolecular effects based on highly organized hydrogen bonds. The SMP can undergo solid-state to solid-state transitions (e.g. a change in morphology). Solid-state to solid-state transitions are well known to those of skill in the art, for example as in poly(styrene-block-butadiene).

An object formed using shape-memory polymers can be prepared to control the direction of change during recovery. In other words, contraction and/or expansion can occur along one or more dimensional axes depending how the polymers are shaped and stressed. For example, in a SMP fiber, the change in shape can be limited to one dimension, such as along the length.

In another embodiment, the thermal and electrical conductivity of the SMP materials can be changed in response to changes in temperature.

The moisture permeability of the compositions can be varied, especially when the polymer is formed into a thin film (i.e., less than about 10 μm). Some polymer compositions, in their original shape, have a sufficient permeability such that molecules of water vapor can be transmitted through the polymer film, while water molecules are not large enough to penetrate the polymer film. The resulting materials have low moisture permeability at temperatures below room temperature and high moisture permeability at temperatures above room temperature.

The polymers can incorporate "hard" and "soft" segments. The segments preferably are oligomers. As used herein, the term "oligomer" refers to a linear chain molecule having a molecular weight up to 15,000 Daltons. The polymers forming the segments are selected based on the desired glass transition temperature(s) (if at least one segment is amorphous) or the melting point(s) (if at least one segment is crystalline), which in turn is based on the desired applications, taking into consideration the environment of use. Preferably, the number average molecular weight of the polymer segment is greater than 400, and is preferably in the range of between 500 and 15,000.

The transition temperature at which the polymer abruptly becomes soft and deforms can be controlled by changing the monomer composition and the kind of monomer, which enables one to adjust the shape-memory effect to give a desired recovery temperature. The thermal properties of the polymers can be detected, for example, by dynamic mechanical thermoanalysis (DMTA) or differential scanning calorimetry (DSC) studies. In addition, the melting point can be determined using a standard melting point apparatus.

The polymers can be thermoset or thermoplastic polymers, although thermoplastic polymers are preferred due to their ease of molding. Thermosets, however, are preferred in some applications, due to their biological and thermomechanical properties.

Preferably, the degree of crystallinity of the polymer or polymeric block(s) is between 3 and 80%, more preferably between 3 and 60%. When the degree of crystallinity is greater than 80% while all soft segments are amorphous, the resulting polymer composition has poor shape-memory characteristics.

The tensile modulus of the polymers below the $T_{trans}$ is typically between 50 MPa and 2 GPa (gigapascals), whereas the tensile modulus of the polymers above the $T_{trans}$ is typically between 1 and 500 MPa. Preferably, the ratio of elastic modulus above and below the $T_{trans}$ is 20 or more. The higher the ratio, the better the shape-memory of the resulting polymer composition.

The polymer segments can be natural or synthetic, although synthetic polymers are preferred. The polymer segments can be biodegradable. In general, these materials degrade by hydrolysis, by exposure to water or enzymes under physiological conditions, by surface erosion, by bulk erosion, or a combination thereof. Non-biodegradable polymers preferably do not include aromatic groups, other than those present in naturally occurring amino acids.

The polymers are selected based on the desired glass transition temperature(s) (if at least one segment is amorphous) or the melting point(s) (if at least one segment is crystalline), which in turn is based on the desired applications, taking into consideration the environment of use. Preferably, the number average molecular weight of the polymer block is greater than 400, and is preferably in the range of between 500 and 15,000 for hard/soft copolymers.

The polymer can be in the form of a hydrogel (typically absorbing up to about 90% by weight of water), and can optionally be ionically crosslinked with multivalent ions or polymers. Ionic crosslinking between soft segments can be used to hold a structure, which, when deformed, can be reformed by breaking the ionic crosslinks between the soft segments. The polymer can also be in the form of a gel in solvents other than water or aqueous solutions. In these polymers, the temporary shape can be fixed by hydrophilic interactions between soft segments.

Representative natural polymer blocks or polymers include proteins such as zein, modified zein, casein, gelatin, gluten, serum albumin, and collagen, and polysaccharides such as alginate, celluloses, dextrans, pullulane, and polyhyaluronic acid, as well as chitin, poly(3-hydroxyalkanoate)s, especially poly(β-hydroxybutyrate), poly(3-hydroxyoctanoate) and poly(3-hydroxyfatty acids). Representative natural biodegradable polymer blocks or polymers include polysaccharides such as alginate, dextran, cellulose, collagen, and chemical derivatives thereof (substitutions, additions of chemical groups, for example, alkyl, alkylene, hydroxylations, oxidations, and other modifications routinely made by those skilled in the art), and proteins such as albumin, zein and copolymers and blends thereof, alone or in combination with synthetic polymers.

Representative synthetic polymer blocks or polymers include polyphosphazenes, poly(vinyl alcohols), polyamides, polyester amides, poly(amino acid)s, synthetic poly (amino acids), polyanhydrides, polycarbonates, polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyvinylpyrrolidone, polyesters, polylactides, polyglycolides, polysiloxanes, polyurethanes and copolymers thereof. Examples of polyacrylates include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate).

Synthetically modified natural polymers include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt. These are collectively referred to herein as "celluloses."

Representative synthetic degradable polymer segments include polyhydroxy acids, such as polylactides, polyglycolides and copolymers thereof; poly(ethylene terephthalate); polyanhydrides, poly(hydroxybutyric acid); poly(hydroxyvaleric acid); poly[lactide-co-(s-caprolactone)]; poly [glycolide-co-(s-caprolactone)]; polycarbonates, poly (pseudo amino acids); poly(amino acids); poly (hydroxyalkanoate)s; polyanhydrides; polyortho esters; and blends and copolymers thereof. Polymers containing labile bonds, such as polyanhydrides and polyesters, are well known for their hydrolytic reactivity. Their hydrolytic degradation rates can generally be altered by simple changes in the polymer backbone and their sequence structure.

Examples of non-biodegradable synthetic polymer segments include ethylene vinyl acetate, poly(meth)acrylic acid, polyamides, polyethylene, polypropylene, polystyrene, polyvinyl chloride, polyvinylphenol, and copolymers and mixtures thereof.

Hydrogels can be formed from polyethylene glycol, polyethylene oxide, polyvinyl alcohol, polyvinyl pyrrolidone, polyacrylates, poly (ethylene terephthalate), poly(vinyl acetate), and copolymers and blends thereof. Several polymeric blocks, for example, acrylic acid, are elastomeric only when the polymer is hydrated and hydrogels are formed. Other polymeric blocks, for example, methacrylic acid, are crystalline and capable of melting even when the polymers are not hydrated. Either type of polymeric block can be used, depending on the desired application and conditions of use. For example, shape-memory is observed for acrylic acid copolymers only in the hydrogel state, because the acrylic acid units are substantially hydrated and behave like a soft elastomer with a very low glass transition temperature. The dry hydrogels are not shape-memory polymers. When dry, the acrylic acid units behave as a hard plastic even above the glass transition temperature and show no abrupt change in mechanical properties on heating. In contrast, copolymers including methyl acrylate polymeric blocks as the soft segments show shape-memory properties even when dry.

Certain polymers, for example, poly(ethylene oxide-co-propylene oxide) block copolymers (PLURONICS™, BASF) are soluble in water at temperatures lower than body temperature and become hydrogels at temperatures higher than body temperature. Incorporation of these polymers as blocks in shape-memory polymers provides the shape-memory polymers with the ability to response to changes in temperature in a manner totally opposite that of typical shape-memory polymers. These materials recover their shape when cooled below their shape recovery temperature, rather than being heated above their shape recovery temperature. This effect is called inversed thermal shape-memory effect. Shape-memory polymer compositions including these polymer blocks are useful in various biomedical applications where the polymer can be inserted as a liquid, and cooled to recover an intended shape in situ. The inverse thermal shape-memory effect can be obtained by incorporating two different blocks into a polymer that are miscible at temperatures lower than $T_{misc}$ but are immiscible at higher temperatures. The phase separation at higher temperatures stabilizes the temporary shape.

Various polymers, such as polyacetylene and polypyrrole, are conducting polymers and such polymers can be used in conjunction with the devices of the present invention.

In a preferred embodiment, the shape-memory polymer composition is able to hold more than one shape in memory. For example, the composition can include a hard segment and at least two soft segments, wherein the $T_{trans}$ of the hard segment is between –30 and 270° C., and is at least 10° C., and preferably 20° C., higher than the $T_{trans}$ of one of the soft segments, and the $T_{trans}$ of each subsequent soft segment is at least 10° C., and preferably 20° C., lower than the $T_{trans}$ of the preceding soft segment. Optionally, one or more of the segments can be biodegradable or linked to another segment via a biodegradable linkage, such as ester-, amide-, anhydride-, carbonate-, or orthoester linkages.

The polymers can be in the form of linear diblock-, triblock-, tetrablock-, or multiblock copolymers, branch or graft polymers, thermoplastic elastomers, which contain dendritic structures, and blends thereof. The thermoplastic shape-memory polymer composition also can be a blend of one or more homo- or co-polymer with one or more diblock-, triblock-, tetrablock-, or multiblock copolymers, branch or graft polymers. These types of polymers are well known to those of skill in the art.

The polymers can be thermoset polymers. There are four different types of thermoset polymers that have shape-memory capability. These include polymer networks, semi-interpenetrating networks, interpenetrating networks, and mixed-interpenetrating networks.

A polymer network is prepared by covalently crosslinking macromonomers, i.e., polymers that contain polymerizable end groups such as carbon-carbon double bonds. The polymerization process can be induced by using light or heat sensitive initiators or by curing with ultraviolet light ("UV-light") without an initiator. Shape-memory polymer networks are prepared by crosslinking one or more soft segments which correspond to one or more thermal transitions.

The shape-memory polymers can exist as physical mixtures of thermoplastic polymers. In one embodiment, a shape-memory polymer composition can be prepared by interacting or blending two thermoplastic polymers. The polymers can be semicrystalline homopolymers, semicrystalline copolymers, thermoplastic elastomers with linear chains, thermoplastic elastomers with side chains or any kind of dendritic structural elements, and branched copolymers, and these can be blended in any combination thereof.

Shape-memory blends can have better shape-memory capabilities than the blend components alone. Shape-memory blends are composed of at least one multiblock copolymer and at least one homo- or copolymer. Di-, tri-, or tetra-block copolymers should be suitable substitutes for a multiblock copolymer.

In a preferred embodiment, the shape-memory polymeric composition includes at least one hard segment and at least one soft segment or multiple soft segments that are covalently crosslinked, wherein at least two of the segments are linked via a functional group which is cleavable under application of light, changes in ionic concentration, changes in pH, electric field, magnetic field, and/or ultrasound. In addition to changing shape in response to changes in temperature, the composition can change its shape in response to application of light, changes in ionic concentration, changes in pH, electric field, magnetic field and/or ultrasound. The temporary shape in these polymers is fixed by the covalent crosslinks.

Various functional groups are known to crosslink in the presence of certain ions or in response to changes in pH. For example, calcium ions are known to crosslink amine and alcohol groups, i.e., the amine groups on alginate can be crosslinked with calcium ions. Also, carboxylate and amine groups become charged species at certain pH's. When these species are charged, they can crosslink with ions of the opposite charge. The presence of groups that respond to changes in the concentration of an ionic species and/or to changes in pH on hard and/or soft segments results in reversible linkages between these segments. One can fix the shape of an object while crosslinking the segments. After the shape has been deformed, alteration of the ionic concentration or pH can result in cleavage of the ionic interactions that formed the crosslinks between the segments, thereby relieving the strain caused by the deformation and thus returning the object to its original shape.

Various materials contain reactive functional groups that fragment in response to applied ultrasound. Examples of these groups are those that form stable radicals, such as nitroso and triphenylmethane groups. One can fix the shape of an object while forming bonds between two or more soft segments, for example by using heat or light. After the shape is deformed, the application of ultrasound can break the bonds between the soft segments, and relieve the strain caused by the deformation. The object will then return to its original shape.

The polymer used to form the segments in the SMP's described above are either commercially available or can be synthesized using routine chemistry. Those of skill in the art can readily prepare the polymers using known chemistry.

The compositions can be formed into a first shape under appropriate conditions, for example, at a temperature above the $T_{trans}$ of the hard segments, and allowed to cool below the $T_{trans}$ of the soft segment(s). Standard techniques are extrusion and injection molding. Optionally, the object can be re-formed into a second shape. Upon application of heat or other appropriate set of conditions, the object returns to original shape.

Thermoset polymers can be prepared by extruding the pre-polymerized material (macromonomers), and fixing the original shape at a temperature above the $T_{trans}$ of the thermoset polymer, for example, by photocuring reactive groups on the monomer. The temporary shape is fixed by cooling the material below $T_{trans}$ after deforming the material.

The crosslinking also can be performed in a solution of the macromonomers. The solvent is removed from the formed gel in a subsequent step.

Those compositions formed of thermoplastic polymers can be blown, extruded into sheets, or shaped by injection molding, for example, to form fibers. The compositions can also be shaped by other methods known to those of skill in the art for shaping solid objects, for example, laser ablation, micromachining, use of a hot wire, and by CAD/CAM (computer aided design/computer aided manufacture) processes. These processes are preferred for shaping thermoplastic polymers.

For several applications it is advantageous to go in small steps from a temporary shape to another temporary shape or the original shape. It is possible to go back and forth between shapes as needed, under the control of an operator.

Usually the $T_{trans}$ of a shape-memory polymer is sharp, so that the polymer can recover its original shape simply by heating the material only a few degrees Celsius. In an alternate embodiment, however, the shape-memory polymer has a broad thermal transition, such that the original shape is fully recovered only when the polymer is heated higher than the upper limit of the thermal transition. A partial recovery occurs when heating at a temperature between the lower and the upper limits of the thermal transition. In this embodiment, the trigger is the temperature, and the effect is essentially independent of the time interval of heat application.

A certain amount of energy needs to be transferred to the shape-memory polymer in order to recover a memorized shape. For the thermal shape-memory effect, the amount of energy required to fully recover a memorized shape depends on the heat capacity of the material. In a preferred embodiment of a thermal shape-memory effect, the polymer has a sharp thermal transition, which is triggered based on the duration the material is exposed to a temperature greater than $T_{trans}$. Other factors affecting the transition include the mass or size of the material, and the temperature and heat transfer coefficient of the medium or environment in contact with (and used to heat) the material. For example, the higher the temperature of the environment, the more quickly the memorized shape is recovered.

In case of the classical thermal shape-memory effect, the entire polymer must be heated by application (and transfer) of heat energy from an external source in order to recover the original shape. In an alternate embodiment, the polymer is heated by energy sources other than temperature. Using these techniques it is possible not only to heat the whole shape-memory device, but also selective parts of the shape-memory device (another way of triggering and enhancing control to recover the original shape).

Polymers absorb light at different wavelengths, depending on their chemical structure. Polymers typically show strong absorption of radiation in the infrared (IR) and near-infrared (NIR) region. The strongest and most suitable absorption ranges for a particular polymer application can be identified using IR or NIR spectroscopy. Shape-memory polymers also can show strong absorption in the ultraviolet (UV) region. The polymer can be cured with light including at least one of the specified frequencies in its spectra, such that the polymer will absorb the light energy and heat up.

The absorption characteristics of the shape-memory polymer can be modified by the addition of a chromophor, which is a moiety, functional group, or molecule showing strong absorption in specific regions of the UV/visible/IR/NIR microwave spectrum. The chromophor can be covalently bound to the polymer, combined as a physical mixture with the polymer, or both.

In a preferred biomedical embodiment, light can be used to non-invasively control an implanted SMP device. For example, the implanted polymer can be cured using specific external light sources that do not simultaneously heat tissue, serum, or other parts of the physiological environment surrounding the SMP implant. Such a light source (e.g., lamp) should emit one or more frequencies of light (e.g., near infrared, "NIR") that are not absorbed by the physiological environment, but which are absorbed by the shape-memory material. The use of NIR light is known in the diagnostics art.

In an alternate embodiment, the technique of interference is applied to control the light frequency applied to an implanted SMP. Interference provides three-dimensional (3-D) control of the region being cured, as the specific frequency of light being absorbed by the shape-memory device is produced at a specified location by the interference of two or more beams crossed at the specified location. The sources of the beams are outside the body, and the frequencies of the beams generally are modulated radio frequencies selected to produce the desired application frequency from the resulting interference.

In an alternate embodiment, gas bubbles or bubble containing liquids, preferably fluorocarbons, are incorporated in the shape-memory device. Using standard ultrasound technology, one can induce a cavitation effect in the gas/liquid to heat the SMP. Techniques for 3-D controlled application of ultrasound are known in the art of biomedical diagnostics.

It is also possible to effect energy transfers based on the interaction of the shape-memory polymer and electromagnetic fields. Use of electromagnetic fields to induce heating or localized temperature changes are well known. In yet another embodiment, energy transfer is produced based on non-radiation effects, such as Foerster-Perrin energy transfer.

Shape-memory polymer compositions can be prepared to have two original (permanent) shapes, i.e. a two-way shape-memory effect. These systems always consist of at least two components. The components are combined by layer techniques (similarly to bimetals) or are interpenetrating networks. By changing the temperature, the shape-memory device changes its shape in the direction of permanent shape 1 or permanent shape 2. Each of the permanent shapes belongs to one component of the device. The shapes of the device always are in equilibrium between both shapes. The temperature dependence of the shape is caused by the fact that the mechanical properties of one component ("component A") are almost independent from the temperature in the temperature interval of interest. The mechanical properties of the other component ("component B") depend on the temperature. In one embodiment, component B becomes stronger at low temperatures compared to component A, while component A is stronger at high temperatures and determines the actual shape. A two-way memory device can be prepared by (a) setting the original shape of component A; (b) deforming the device into original shape of component B; and (c) fixing an original shape of component B while applying a stress to the component.

The recovery of the original shape of a shape-memory polymer can be initiated by a hydrolytic degradation process. In a preferred embodiment, this feature is incorporated into a system including a thermoplastic polymer composed of a hard segment and at least one soft segment or a thermoset containing at least one soft segment (single component systems). In these polymers, two soft segments can be linked by a readily hydrolyzable bond. The term "readily hydrolyzable bond" is used herein to refer to groups having a hydrolysis rate that is greater than that for other functional groups in the polymer. The original shape of these polymers is determined by the hard segments (thermoplastic material) or the covalent crosslinks (thermoset). The temporary shape is fixed by the crosslinks between two soft segments after deforming the device. When the crosslinks between the soft segments are hydrolyzed, the original shape will be recovered. Readily hydrolyzable functional groups include activated ester bonds, such as glycolyl glycolate, and anhydride bonds.

In another preferred embodiment, the polymer is a two-component system in which at least one component is a covalent network, such as an IPN, a mixed-IPN, or a semi-IPN. The covalent network is an amorphous network having a very low $T_{trans}$. The covalent network determines the original shape of the system, and the second component deforms the system to fix the temporary shape. The second component is another network in the case of an IPN, a homo- or co-polymer in the case of a semi-IPN, and a thermoplastic elastomer in the case of a mixed-IPN. The first component (covalent network) hydrolyzes more slowly than the second component, such that the polymer recovers its original shape when the second component is degraded.

Shape-memory polymer compositions, articles of manufacture thereof, and methods of preparation and use thereof are described. In a preferred embodiment, the shape-memory polymer composition can hold more than one shape in memory. For example, the composition can include a hard segment and at least two soft segments. The $T_{trans}$ of the hard segment is at least 10° C., and preferably 20° C., higher than the $T_{trans}$ of one of the soft segments, and the $T_{trans}$ of each subsequent soft segment is at least 10° C., and preferably 20° C., lower than the $T_{trans}$ of the preceding soft segment. A multiblock copolymer with a hard segment with a relatively high $T_{trans}$ and a soft segment with a relatively low $T_{trans}$ can be mixed or blended with a second multiblock copolymer with a hard segment with a relatively low $T_{trans}$ and the same soft segment as that in the first multiblock copolymer. Since the soft segments in both multiblock copolymers are identical, the polymers are miscible in each other when the soft segments are melted. The resulting blend has three transition temperatures: one for the first hard segment, one for the second hard segment, and one for the soft segment. Accordingly, these materials are able to memorize two different shapes.

Any polymers that are crystalline or amorphous and that have a $T_{trans}$ within the range defined herein can be used to form the hard and soft segments. The melting point or glass transition temperature (hereinafter, the $T_{trans}$) of the hard segment is at least 10° C., and preferably 20° C., higher than the $T_{trans}$ of the soft segment. The $T_{trans}$ of the hard segment is preferably between −30 and 270° C., and more preferably between 30 and 150° C. The ratio by weight of the hard segment:soft segment is between about 5:95 and 95:5, preferably between 20:80 and 80:20.

In some embodiments, the shape-memory polymers contain at least one physical crosslink (physical interaction of the hard segment) or contain covalent crosslinks instead of a hard segment. The shape-memory polymers also can be interpenetrating networks or semi-interpenetrating networks. In addition to changes in state from a solid to liquid state (melting point or glass transition temperature), hard and soft segments can undergo solid-to-solid-state transitions, and can undergo ionic interactions involving polyelectrolyte segments or supramolecular effects based on highly organized hydrogen bonds.

Articles of manufacture can be prepared from the shape-memory polymer compositions, for example, by injection molding, blowing, extrusion, laser ablation, micromolding techniques (e.g. using a photomask), and UV resist for use in making a micromold. To prepare an object having a shape in memory, the object can be formed at a temperature above the $T_{trans}$ of the hard segment, and cooled to a temperature below the $T_{trans}$ of the soft segment. If the object subsequently is formed into a second shape, the object can be returned to its original shape by heating the object above the $T_{trans}$ of the soft segment and below the $T_{trans}$ of the hard segment.

Articles of manufacture with two or more shapes in memory can be prepared by forming a polymer composition with a hard segment, a first soft segment, and a second soft segment, where the first soft segment has a $T_{trans}$ at least 10° C. below that of the hard segment and at least 10° C. above that of the second soft segment. After the composition is shaped at a temperature above the $T_{trans}$ of the hard segment, it can be cooled to a temperature below that of the $T_{trans}$ of the first soft segment and above that of the second soft segment and formed into a second shape. The composition can be formed into a third shape after it has been cooled below the $T_{trans}$ of the second soft segment. The composition can be heated above the $T_{trans}$ of the second soft segment to return the composition to the second shape. The composition can be heated above the $T_{trans}$ of the first soft segment to return the composition to the first shape. The composition can also be heated above the $T_{trans}$ of the hard segment, at which point the composition loses the memory of the first and second shapes and can be reshaped using the method described above.

Thermoset polymers can be prepared by pre-shaping macromonomers, for example, by extrusion, and fixing the original shape at a temperature above the $T_{trans}$ of the thermoset polymer, for example, by photocuring reactive groups on the macromonomer. The original shape, however, can only be programmed one time.

In a preferred embodiment, the shape change occurs in response to a change in temperature. In another embodiment, however, the composition can change its shape in response to application of light, changes in ionic concentration and/or pH, electric field, magnetic field or ultrasound. For example, a SMP can include at least one hard segment and at least one soft segment, wherein at least two of the segments, preferably two soft segments, are linked to each other via a functional group that is cleavable under application of light, electric field, magnetic field or ultrasound. The temporary shape is fixed by crosslinking the linear polymers. By cleaving those links the original shape can be recovered. The stimuli for crosslinking and cleaving these bonds can be the same or different.

Deployment of bioresorbable electrodes with or without shape-memory polymer with different deployment characteristics (force and rate) can be achieved through: choice of polymer, the addition of a second phase (co-polymer or polymer blend), degree of cross-linking and via the incorporation of a second phase of nanoparticulates or nanofibers. SMP electrodes can deploy nanoparticulates, nanofibers, microwires, and nanowires with improved electrical properties. Microwires and nanowires can be coated with alumina using atomic layer deposition (ALD) in order to insulate the surface of the electrode, except at the tip. The coating of the present invention enables the use of ductile metal microwires and nanowires that would buckle when inserted alone. Further, the use of bioresorbable polymers with or without shape-memory effects can be used to deploy microwire and nanowire electrodes in tissue leaving the wire suspended following resorption. This slow deployment (minutes to days) of electrodes of other materials can be used to minimize tissue reactivity leading to improved long-term performance. The reactivity is lessened in that the SMP's are slowly resorbed into the tissue and thus gradually expose the electrodes to the tissue. The gradual exposure lessens the immune response to the electrodes. Additionally, the SMPs can be useful in limiting, or eliminating, micromovement.

The surface morphology of the electrode or coating can be modified in the nano and micro scale to modify the interaction of the electrodes with surrounding tissue. The surface can be modified using techniques known to those of skill in the art. Examples of such techniques include, but are not limited to, chemically scuffing or altering the surface, mechanical scuffing of the surface, and nanotexturing the surface during fabrication or post-fabrication. Such changes are broadly referred to as "surface engineering", which can include chemical, structural, or morphological changes to the surface of the electrode or coating.

Biologicals or chemicals can be incorporated into the bioresorbable electrodes that can be released upon resorption to modify tissue reactivity, promote or inhibit cell and extracellular matrix adhesion or to serve as a biological tracer of insertion site. Timing of release can be tailored by changing the properties of the bioresorbable polymer. Biologicals or chemicals can be incorporated on the surface of shape-memory polymer electrodes that can be released or directly interact with surrounding tissue to modify tissue reactivity and promote or inhibit cell and extracellular matrix adhesion. Examples of such material include, but are not limited to, immunosuppressive compounds and agents. Immunosuppressive agents are defined as agents that suppress immune responses. The agents can include, but are not limited to, immunoprotective cells, such as Sertoli cells, stem cells, stem cell by-products, or other compounds that create an immunosuppressive effect. Examples of such immunosuppressive compounds include, but are not limited to, PKC inhibitors, glutamate receptor inhibitors, cyclosporins, FK506, corticoseroids, and ascomycins. A glutamate receptor inhibitor is defined as any of a class of pharmacological agents, which prevent the binding and/or action of glutamate (or glutamatergic agonists) at ionotropic or metabotropic glutamate receptors, resulting in reduced or completely blocked transduction by such receptors.

Additionally, the coating can be used in conjunction with a bioresorbable scaffolding. The scaffolding enables the nanowires to be inserted without affecting the surrounding tissue. Then, as the scaffolding is resorbed into the tissue, the nanowires are slowly exposed to the tissue, thus lessening the immune response to the nanowires.

The SMP's of the present invention can also be placed on other objects. For example, the SMP's of the present invention can be placed on an exterior surface of biological sensors. When the SMP's are placed on a biological sensor the sensor is better able to detect biological materials and chemicals in the body because the sensor is disguised by the SMP's and is thus not recognized by the body as being a foreign object.

Further, the SMP's of the present invention can be placed on artificial parts placed within the body. For example, the SMP's can be placed on an artificial knee. The benefit of the SMP's is that the body does not recognize the artificial knee as being foreign and thus shortens the healing process.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

Insertion of electrodes in brain tissue evokes an inflammatory astrocytic scar reaction that severely limits long-term electrode performance. The rate of electrode insertion and the composition of electrode coatings are major factors contributing to the astrocytic scar. The use of low modulus, compliant materials capable of slow deployment in situ minimizes adverse long-term tissue reactivity to electrode implantation. In order to deploy electrodes in situ at slow rates (hours to days), thermally actuated composite electrodes fabricated from shape-memory polymers (SMP's) were used. SMP's were designed to deploy at body temperature at different rates, thereby enabling a thorough study of the effect of rate of deployment on the extent of astrocytic scar reaction. Composite SMP electrodes incorporated compliant gold conductors and were attached to a base of lightweight polyimide. Different coatings of the tip of the electrode were tested for biocompatibility, including bioresorbable coatings. The extent of the astrocytic scar reaction, necrosis, microgial infiltration and apoptosis were determined by immunohistochemistry. Long-term electrode reliability was quantified by recording and/or stimulating single unit responses at different times post-implantation. Changes in electrical parameters were correlated to changes in the astrocytic scar reaction.

Example 2

Shape-Memory Polymers

Shape-memory polymers (SMP's) and SMP composites (Gall et al., 2002; Tobushi et al., 1992) are an attractive compliant material that has not been proposed for use in electrodes. The thermo-mechanical response of shape-memory polymers is shown schematically in FIG. 1, as defined by four critical temperatures. The glass transition temperature, $T_g$, is the reference point for thermo-mechanical deformation and recovery. An advantage of SMP's is that $T_g$ can be easily varied over a temperature range of several hundred degrees by control of chemistry or degree of cross-linking. The deformation temperature, $T_d$, is the temperature at which the polymer is deformed into its temporary shape (FIG. 1). The initial deformation at $T_d$ can occur above or well below $T_g$ depending on the desired recovery response (Gall et al., 2002). The storage temperature, $T_s$, is below $T_d$ and constitutes the temperature at which the temporary shape is stable over time. After deformation at $T_d$, the material is typically cooled to $T_s$ with varying degrees of strain/stress constraint ranging from no constraint to full constraint (FIG. 1). The recovery temperature, $T_r$, represents the temperature range at which the material recovers its original shape during heating. Recovery can be accomplished isothermally by heating to a fixed $T_r$ and then holding, or by continued heating up to and past $T_r$ (Gall et al., 2002; Liu et al., 2003).

Because these polymers can be fabricated to the micrometer scale using photolithographic techniques, this allows for reproducible fabrication of compliant electrodes. Further, by adding different materials it is possible to control the actuation force and rate of deployment (minutes to hours), making it possible to deploy the electrode in a minimally invasive manner. Although not intrinsically conductive, SMP's can be fabricated with microwire inclusions or can have evaporated conductive wires patterned on the surface using electron beam evaporated gold.

One of the major limitations of present technology in implantable electrodes is poor long-term biocompatibility and degradation of electrical reliability. Ideally, an implanted electrode should not impact the surrounding cells thereby providing for stable long-term recording and/or stimulation of extracellular field potentials from neighboring neurons. Electrode materials should be compliant thereby minimizing differential movement of the electrode with respect to brain tissue. However, immediately upon insertion of microwire or silicon micromachined electrodes, there is tissue inflammation and necrotic cell death. Interestingly, the quality of recording and/or stimulation from chronic microwire electrodes increases in the first few days of recording and/or stimulation, likely due to decrease in tissue inflammation and edema. However, a longer-term reactive astrocytic reaction ensues that result in physical blockage of the electrode by a surrounding sheath of reactive astrocytes. The "astrocytic scar" as well as corrosion of the electrode surface contribute to progressive signal degradation (Maynard et al., 2000; Nadol, Jr. et al., 2001; Rousche et al., 2001; Rousche and Normann, 1998; Turner et al., 1999; Williams et al., 1999). Two components of the astrocytic tissue reaction, short-term and long term, have been described. It has been postulated that electrode geometry and device size influence only the short term reaction. The implication being that the long term reactions are exclusively due to material biocompatibility (Szarowski et al., 2003). Additionally, micromovement can also affect biocompatibility. While this conclusion is likely correct for the conditions tested in the Szarowski manuscript, the range of electrode cross-sections tested was limited, and bioresorbable materials were not used in that study. In addition, a causal relationship between the long-term and short-term reactions cannot be discarded in that study because the short-term reaction was significant under all conditions tested in that study.

The causal relationship between the initial necrosis and subsequent inflammation and astrocytic scar is not well understood for electrode insertion. Brain stab wound, a process with significant parallels to electrode insertion injury, is much better understood. Studies of brain stab injury indicate that the insertion of a sharp foreign object into brain tissue elicits blood spillage and cell necrosis thereby causing large increases in the concentration of glutamate, a molecule that is normally used by the central nervous system as a neurotransmitter, but becomes exitotoxic at high concentration. Glutamate causes exitotoxicity in neurons promoting further necrosis and triggering an inflammatory reaction with recruitment of microglia, the immune cells of the nervous system. Within a few days signaling molecules released by the microglia, presumably cytokines, elicit formation of an "astrocytic scar" formed of reactive astrocytes surrounding the wound. In parallel, and perhaps mediated through microglia activation, there is a slower development of apoptosis (programmed cell death) in a period of days to weeks (Beattie et al., 2000; Citron et al., 2000; Eldadah and Faden, 2000; Giulian et al., 1989; Knoblach et al., 2002; Krum et al., 2002; Roitbak and Sykova, 1999; Snider et al., 1999; Turner et al., 1999; Tzeng and Wu, 1999).

Several aspects of tissue response to stab wound are problematic for long-term measurement with microelectrode arrays. Astrocytic scars are an electrical barrier between the electrodes and the neighboring neurons, resulting in decreased signal-to-noise ratio. In addition, given that there is little adult neurogenesis, neuronal apoptosis causes irreversible loss of the source of electrical signals. It is therefore extremely important to decrease the magnitude of the inflammatory reaction to electrode insertion. A major hypothesis in stab brain injury is that the adverse reaction to the stab is triggered by large increases in glutamate concentration that cannot be handled by normal glutamate homeostasis mechanisms. Since a major source of glutamate is spillage from injured cells and damaged blood vessels in the electrode insertion path, slow rates of insertion (hours to days) results in a smaller increase in glutamate concentration and in a diminished tissue reaction. This in turn leads to improved long term performance of electrodes.

Bioresorbable Polymers.

Polyesters based on polylactic acid (PLA), polyglycolic acid (PGA) and their copolymers are the most commonly used materials for their bioresorbable characteristics. They are biocompatible and FDA approved (for a particular form of synthesis) (Vert et al., 1998). While the mechanisms of hydrolytic degradation are complex, the rate of degradation ranging from weeks to months can be controlled either through composition as in forming polymer blends or through the addition of initiators. The breakdown products of PLA and PGA are L- or D-lactic and glycolic acid respectively (Ignatius and Claes, 1996), all of which are normally present in the human body. These are typically metabolized by cells surrounding the material by means of the citrate cycle yielding carbon dioxide which is finally eliminated by respiration (Brandt et al., 1984). The combination of bioresorbability and shape-memory effect has been studied by (Lendlein and Langer, 2002) based on a linear, phase-segregated multiblock copolymer as the structural concept with successful results in terms of cyclic thermomechanical properties showing deployment at 37° C. and with linear mass loss of around 50% in 300 days.

Typically, electrodes and arrays are pneumatically inserted into tissue either with a micromanipulator over seconds to minutes or with a pneumatic gun in milliseconds. While pneumatic insertion helps ensure complete insertion of arrays, the biocompatibility of this process has never been directly compared to insertion over seconds to minutes. Deployment of electrodes slowly over the course of hours improves biocompatibility relative to both typical methods. However, if slow deployment were performed using a micromanipulator, patients would have to be kept under anesthesia for long periods of time thereby increasing the risk of death. The use of shape-memory polymers to slowly deploy electrodes over the course of hours or longer eliminates the need to maintain the individuals under anesthesia during the electrode deployment.

Embedded SMP electrodes can be sectioned for histological processing in olfactory bulb in situ. Complete analysis of the tissue response to electrode insertion ideally includes the histological examination of the brain with the electrode in situ. Most studies remove the implant prior to sectioning of the tissue. Alternatively, some investigators perform the laborious task of attempting to section parallel to implants in order not to disrupt the tissue when the sectioning knife contacts the implant material. The present invention instead enables fine wires (<25 μm) to be sectioned or embedded without disrupting the tissue.

Individual wires (25 μm diameter) or embedded SMP electrodes were inserted into the olfactory bulbs of mice immediately after euthanasia. The bulbs were then removed, immersion fixed and prepared for cryosectioning (18 μm sections). It was not possible to section any of the wires tested (stainless steel, Pt, Pt/Ir, Au, Ag, Ni) without some damage to the tissue. However, the softer metals (e.g. Au and Ag, FIG. 2(a)) sectioned, albeit with some tearing. Gold and silver wires that were embedded in SMP were routinely cut without causing tissue disruption (FIG. 2(b)). Generally, the SMP remained attached to the tissue section after processing. The ability for the embedded SMP's to remain adhered to the tissue during processing increases the ability to properly analyze the tissue response due to implantation of novel electrode materials.

Initial Characterization of Biocompatibility of SMP Electrodes.

FIG. 3 shows a cross section of an olfactory bulb one week after implantation with an SMP beam. The section was reacted with an antibody to GFAP, a selective marker of astrocytes, and counter stained with hemotaxolin and eosin. The implant caused gross disruption of tissue histology including a massive infiltration of astrocytes around it. Additionally, slight increases in the number of microglia and apoptotic cells were detected. The extent of astrocytic scaring appears less than that reported for Si micromachined electrodes (Szarowski et al., 2003). Further, examination of an olfactory bulb two weeks after implantation (FIG. 4) shows less astrocytosis compared to one week post-implantation (FIG. 3). A decrease in astrocytosis with time was not evident in studies with Si micromachined electrodes (Szarowski et al., 2003), and indicates better biocompatibility for SMP implant materials.

In order to explore the possibility that slow rates of implant insertion might cause decreased tissue reactivity, the astrocytic scaring resulting one week after insertion of a rapidly inserted SMP beam (~1 mm/sec, FIG. 3) was compared to an embedded gold microwire SMP electrode inserted more slowly (1 mm/40 min, FIG. 5) using an electronically controlled micromanipulator. The slowly deployed embedded SMP electrode caused very little astrocytic scarring. This establishes that slow insertion of implants reduces the extent of damage to the tissue. Thermally actuated SMP electrodes that deploy over the course of many hours or days actually induces even less tissue damage.

Figure 6A:
FIGS. 6A and 6B show force measurement.
Figure 6B:
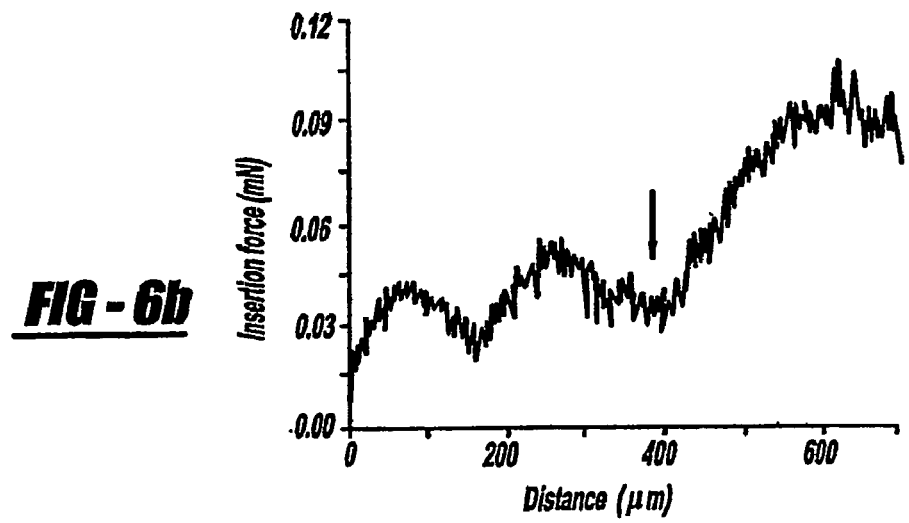
Figure 7A:
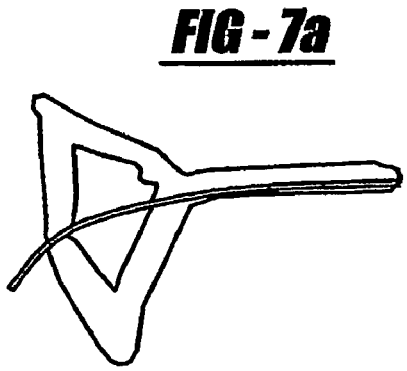
Figure 7A:
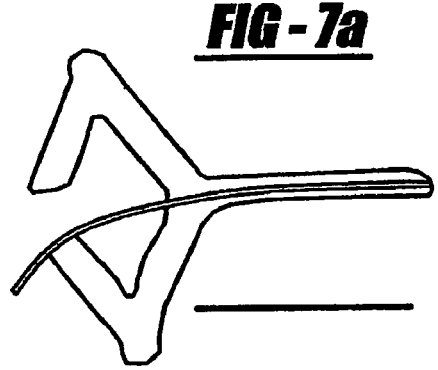
Figure 7C:
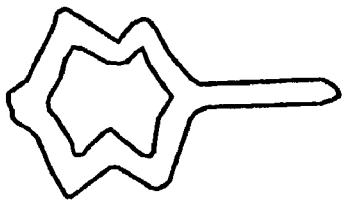
Figure 7D:
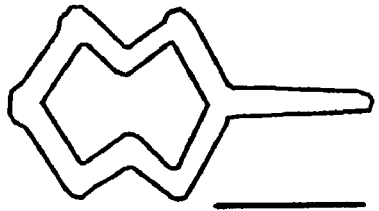

FIG. 6(a) shows the tip of an SMP electrode without an embedded microwire partially inserted into a mouse olfactory bulb. Force of insertion was measured at NIST on the basis of Hooke's law using a piezoelectric actuator specifically designed to measure force in the 5 μN-100 mN range. The SMP materials were capable of providing sufficient stiffness to avoid kinking or buckling of the electrode as they were inserted into the mouse olfactory bulb even without the presence of the microwire for added rigidity. FIG. 6(b) shows the force of insertion as a function of distance. The magnitude of the insertion forces measured in mouse olfactory bulb (ca 40 μN) are consistent (after scaling for probe size) with forces measured in pig brain (ca 100 mN)(Miller et al., 2000). Forces measured in olfactory bulb are several orders of magnitude below the mN forces that can be generated by SMP materials (Gall et al., 2002). SMP materials are capable of generating enough force for deployment in the brain following surgical implantation.

FIG. 7 shows two designs for linear actuators, one with an embedded 25 μm gold conductor. In the initial tests linear deployments of 280 μm (FIG. 7(b)) and 170 μm (FIG. 7(d)) were obtained. Deployment of 500 μm is also obtainable.

Shape-Memory Effect of Bioresorbable PGA Polymers.

An initial attempt has been made to evaluate the shape-memory effect of bioresorbable PGA. Heating the polymer from the solid-state and applying a compressive force at 120° C. prior to cooling to room temperature shows the polymer retains the deformed pattern. Although the shape-memory effect is weaker than that exhibited by epoxy based materials, initial measurements show that re-heating the PGA polymer results in recovery (FIG. 8). These results are extremely encouraging since increasing the $T_g$ by way of adding a second phase (e.g. blending with Poly Lactic Acid (PLA)) or cross-linking of the PGA polymer has a significant impact on the force of recovery.

Figure 2A:
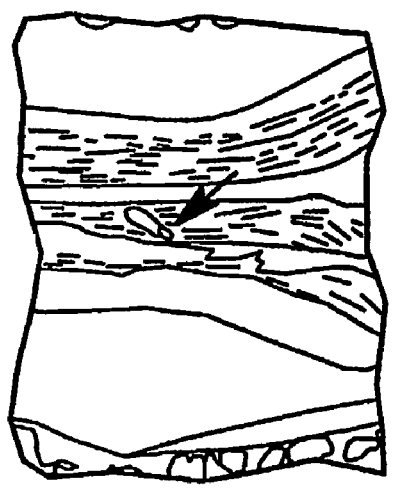
FIGS. 2A and 2B are photographs of sections of olfactory bulb with (FIG. 2A) 25 μm gold microwire or (FIG. 2B) embedded shape-memory polymer (SMP)/gold electrode (150×300 μm); scale bar 300 μm, arrows point to gold microwire.
Figure 2B:
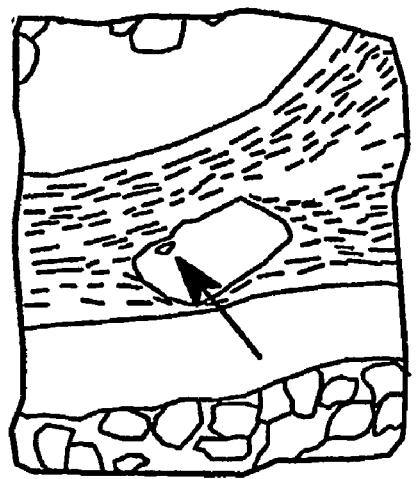

FIG. 1 is a schematic of the shape-memory effect in polymers as defined by four critical temperatures. The value of $T_g$ is a material property that can be altered depending on the application. Typically, $T_s$ is always less than $T_g$, while $T_d$ can be above or below $T_g$, depending on the desired recovery response. The value of $T_r$ depends on both $T_d$ and $T_g$;

FIG. 2 shows sections of olfactory bulb with (FIG. 2a) 25 μm gold microwire or (FIG. 2b) embedded SMP/gold electrode (150×300 μm). Implant in (FIG. 2b) appears somewhat larger than the actual dimensions due to the angle of sectioning, the scale bar is 300 μm and arrows point to gold microwire.

FIG. 3 shows the tissue response to implantation of 100× 200 μm SMP one week post-implantation. Implanted olfactory bulb (FIG. 3a) showed a large infiltration of astrocytes stained for GFAP (brown) around the implant compared to the contralateral bulb (FIG. 3b), the scale bar is 200 μm.

FIG. 4 shows the tissue response to implantation of 100× 200 μm SMP after two weeks. The astrocytic scar around the implant in (FIG. 4a) is smaller and less dense than that for a one week implant (FIG. 3). Note that the shape and size of the implant are odd due to the severe misalignment of the bulb before sectioning. FIG. 4b shows the section through the control contralateral bulb, the scale bar is 200 μm.

FIG. 5 shows the tissue response to a one week "slowly" (1 mm/40 minutes) inserted SMP/gold wire implant (75×200 μm). The implanted bulb (FIG. 5a) showed an increase in astrocytes around the implant when compared to the control bulb (FIG. 5b), but the extent of the astrocytic scar was less then that seen for rapidly inserted implants (FIGS. 3,4). Notice that the presence of astrocytes in midline is a normal feature of the bulb.

FIG. 6 shows the force measurement, wherein the top digital micrograph of an SMP beam partially inserted into the olfactory bulb (on left) and the bottom is a force-displacement graph. Taper was entirely covered at 400 μm, where the slope relates to the friction of insertion reaching a maximum of 0.1 mN.

FIG. 7 shows two different designs (FIGS. 7a and b, and FIGS. 7c and d) for SMP linear actuators with 25 μm embedded gold wire in the compressed state (FIGS. 7 (a) and (c)) and following thermal actuation (FIGS. 7 (b) and (d)), the bars are 1 mm.

FIG. 8 shows the shape-memory effect in poly glycolic acid (PGA), (FIG. 8a) the shape after deformation at 120° C., and (FIG. 8b) subsequent recovery above $T_g$, the bar is 1 mm.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method for inserting an electrode into tissue by inserting a slowly implantable electrode comprising a share-memory polymer coated electrode capable of being slowly implanted into brain tissue.

2. The method according to claim 1, wherein said inserting step includes inserting the electrode into tissue and slowly resorbing a coating on the electrode into the brain.

3. The method according to claim 1, wherein said inserting step includes slowly placing the electrode within the tissue to be treated.

4. The method according to claim 1, further including altering surface structure of the electrode.

5. A method of minimizing trauma and astrocytic scarring by slowly inserting a slowly implantable electrode comprising a share-memory polymer coated electrode capable of being slowly implanted into body tissue, thereby minimizing trauma and astrocytic scarring.

6. The method according to claim 5, wherein said inserting step includes inserting the electrode into body tissue and slowly resorbing a coating on the electrode into the tissue.

7. A method of minimizing trauma and astrocytic scarring by slowly inserting a slowly implantable electrode comprising a shape-memory polymer coated electrode and having a therapeutic coating into body tissue and allowing the body to absorb the therapeutic coating to minimize trauma and astrocytic scarring.

* * * * *